United States Patent [19]

Stridde

[11] 4,046,826
[45] Sept. 6, 1977

[54] PROCESS FOR ALKYLATING AROMATIC HYDROCARBONS WITH SYNTHETIC HECTORITE-TYPE CLAY CATALYST

[75] Inventor: George E. Stridde, Houston, Tex.

[73] Assignee: N L Industries, Inc., New York, N.Y.

[21] Appl. No.: 698,104

[22] Filed: June 21, 1976

Related U.S. Application Data

[60] Division of Ser. No. 530,092, Dec. 6, 1974, Pat. No. 3,979,331, which is a continuation-in-part of Ser. No. 503,985, Sept. 6, 1974, Pat. No. 3,965,043.

[51] Int. Cl.² .................... C07C 3/52; C07C 15/09
[52] U.S. Cl. .................................. 260/671 C
[58] Field of Search ......................... 260/671 C

[56] References Cited

U.S. PATENT DOCUMENTS

| 3,962,361 | 6/1976 | Stridde | 260/671 C |
| 3,965,043 | 6/1976 | Stridde | 252/455 R |
| 3,979,331 | 9/1976 | Stridde | 252/454 |
| 3,992,467 | 11/1976 | Stridde | 260/671 C |

Primary Examiner—Delbert E. Gantz
Assistant Examiner—J. Thierstein

[57] ABSTRACT

Alkylatable aromatic hydrocarbons are alkylated with olefins and alkylhalides under anhydrous alkylating conditions in the presence of certain metallic cation exchanged synthetic hectorite-type catalysts in which the metallic cation has a Pauling electronegativity greater than 1.0 and in which the central octahedral layer contains one or more divalent metals which have an ionic radius not greater than 0.75 A. In a specific embodiment, 1-dodecene is reacted with benzene by contacting the dodecene and benzene under anhydrous alkylating conditions in the liquid phase at the boiling point of the mixture with a catalyst comprising a metallic cation such as $Al^{3+}$, $In^{3+}$, and $Cr^{3+}$ exchanged onto the surface of a synthetic nickeliferous hectorite.

17 Claims, No Drawings

PROCESS FOR ALKYLATING AROMATIC HYDROCARBONS WITH SYNTHETIC HECTORITE-TYPE CLAY CATALYST

This is a division of application Ser. No. 530,092, now U.S. Pat. No. 3,979,331, filed Dec. 6, 1974 which is a continuation-in-part of application Ser. No. 503,985 filed Sept. 6, 1974, now U.S. Pat. No. 3,965,043.

This invention relates to a process for the liquid phase alkylation of aromatic hydrocarbons in which the catalyst comprises certain cation-exchanged synthetic hectorite-type clays. More particularly, the present invention is concerned with a method wherein an aromatic hydrocarbon, e.g. benzene, and an alkylating agent, e.g. an olefin, are reacted in the liquid phase in the presence of a catalyst which comprises a synthetic hectorite-type mineral which has a metal cation having a Pauling electronegativity greater than 1.0 in ion-exchange positions on the surface of the clay particles, and in which the central octahedral layer contains one or more divalent metals having an ionic radius not greater than 0.75 A as more particularly described hereinafter. Alkylated aromatic hydrocarbons have many uses depending on their molecular weight and structure. Thus low molecular weight alkylbenzenes are useful in high octane gasolines and high molecular weight alkylbenzenes are useful as intermediates in the production of alkylbenzene sulfonate detergents.

It has been reported that various materials containing acidic catalytic sites are useful in catalyzing the reaction between aromatic hydrocarbons and various alkylating agents such as olefins and alkyl halides. See for example: The Kirk-Othmer Encyclopedia of Chemical Technology, 2nd Edition, Vol. 1, pp. 882–901 (1963); "Alkylation of Benzene with Dodcene-1 Catalyzed by Supported Silicotungstic Acid," R. T. Sebulsky and A. M. Henke, Ind. Eng. Chem. Process Res. Develop., Vol. 10, No. 2, 1971, pp. 272–279; "Organic Molecule and Zeolite Crystal: At the Interface," P. B. Venuto, Chem. Tech., April, 1971, pp. 215–224; "Catalysis by Metal Halides, IV. Relative Efficiencies of Friedel-Crafts Catalysts in Cyclohexane-Methylcyclopentane Isomerization, Alkylation of Benzene and Polymerization of Styrene", G. A. Russell, J. Am. Chem. Soc., Vol. 81, 1959, pp. 4834–4838.

It has also been proposed to use various modified clays as catalysts in various acid catalyzed reactions such as alkylation, and the like. See for example the following U.S. Pat. Nos.: 3,665,778; 3,665,780; 3,365,347; 2,392,945; 2,555,370; 2,582,956; 2,930,820; 3,360,573; 2,945,072; 3,074,983. The latter patent is the only patent known to me which discloses the use of hectorite clay as a catalyst. Other references which disclose the use of clays as catalysts are as follows: "Acid Activation of Some Bentonite Clays", G. A. Mills, J. Holmes and E. B. Cornelius, J. Phy. & Coll. Chem., Vol. 54, pp. 1170–1185 (1950); "H-Ion Catalysis by Clays", N. T. Coleman and C. McAuliffe, Clays and Clay Minerals, Vol. 4, pp. 282-14 289 (1955); "Clay Minerals as Catalysts:", R. H. S. Robertson, Clay Minerals Bull. Vol. 1, No. 2, pp. 47–54 (1948); "Catalytic Decomposition of Glycerol by Layer Silicates", G. F. Walker, Clay Minerals, Vol. 7, pp. 111–112 (1967); "Styrene Polymerization with Cation-Exchanged Alumino-silicates", T. A. Kusnitsyna and V. M. Bromolko, Vysokomol. Soedin., Ser. B1968, Vol. 10, No. 10, pp. 776–9 — see Chem Abstracts 70:20373x (1969); "Reactions Catalyzed by Minerals. Part I. Polymerization of Styrene:, D. H. Solomon and M. J. Rosser, J. Applied Polymer Science, Vol. 9, 1261–1271 (1965).

The structure of hectorite-type minerals is well known. See for example the following publications, incorporated herein by reference: "Clay Mineralogy", R. E. Grim, Chapter 4, 2nd Edition (1968). McGraw-Hill Book Co.; "Rock-Forming Minerals. Vol. 3. Sheet Silicates:, W. A. Deer, R. A. Howie, and J. Zussman, 226–245 (1962). John Wiley and Sons, Inc. The following references incorporated herein by reference, describe processes for the hydrothermal synthesis of smectite-type minerals: "A Study of the Synthesis of Hectorite", W. T. Granquist and S. S. Pollack. Clays and Clay Minerals, Proc. Nat'l. Conf. Clays Clay Minerals. 8,150–169 (1960); "Synthesis of a Nickel-Containing Montmorillonite", B. Siffert and F. Dennefeld. Comptes Rendus Acad. Sci., Paris, Ser. D. 1968, 267 (20), 1545–8 (Reference Chemical Abstracts, Vol. 70; 43448q); "Synthesis of Clay Minerals", S. Caillere, S. Henin, and J. Esquevin. Bull. groupe franc.argiles. 9, No. 4, 67–76 (1957) (Reference Chemical Abstracts 55: 8190e); U.S. Pat. No. 3,586,478; U.S. Pat. No. 3,666,407; U.S. Pat. No. 3,671,190; "Synthesis of Zinciferous Montmorillonite:", J. Esquevin. Comptes Rendus, Acad. Sci., Paris, 241, 1485–6 (1955); "Synthesis of Clay Minerals at Low Temperatures":, S. Henin. Natl. Acad. Sci.- Natl. Research Council Publ. No. 456, 54–60 (1956); "Synthesis of Nickel Hydrosilicates", P. Franzen and J. J. B. van Eijk van Voorthuysen. Trans. 4th Int. Congress Soil Sci., Amsterdam 3:34–7, 4:64 (1950).

I have now found that certain synthetic trioctahedral 2:1 layer-lattice smectite-type minerals, particularly certain synthetic hectorite-type minerals, which have had their exchangeable cations replaced with a metallic cation having a Pauling electronegativity greater than 1.0 are effective catalysts for the alkylation of alkylatable aromatic hydrocarbons, e.g. benzene, with an olefin or alkyl halide under anhydrous alkylating conditions in the liquid phase.

Accordingly, it is an object of this invention to provide a process for alkylating in the liquid phase an alkylatable aromatic hydrocarbon with an olefin or alkyl halide under anhydrous alkylating conditions in the presence of certain synthetic hectorite-type catalysts in which the central octahedral layer contains one or more divalent metals having an ionic radius not greater than 0.75 A and which has in its cation exchange positions a metallic cation having a Pauling electronegativity greater than 1.0. It is another object of this invention to provide a method of alkylating aromatic hydrocarbons which comprises contacting in the liquid phase an alkylatable aromatic hydrocarbon with an olefin or alkyl halide in a reaction zone which is substantially free of water and in the presence of an effective amount of a catalyst, said catalyst comprising certain metallic cation exchanged synthetic hectorite-type clays wherein the metallic cation has a Pauling electronegativity greater than 1.0 and in which the central octahedral layer contains one or more divalent metals having an ionic radius not greater than 0.75 A. Another object is to provide a new catalyst which comprises a metallic cation exchanged synthetic hectorite-like clay in which the central octahedral layer contains one or more divalent metals having an ionic radius not greater than 0.75 A, provided that said octahedral layer contains less than 95 mole percent Mg, wherein the metallic cation has a Pauling electronegativity greater than 1.0. Other objects and advantages of this invention will become apparent to those skilled in the art upon reading the disclosure and the appended claims.

The catalyst of this invention comprises (1) a metallic cation which has a Pauling electronegativity greater than 1.0 exchanged onto the surface of (2) certain synthetic trioctahedral 2:1 layer-lattice smectite-type minerals in which the central octahedral layer contains one or more divalent metals having an ionic radius not greater than 0.75 A as described hereinafter.

Representative metallic cations which are useful in this invention may be derived from the following metals, the Pauling electronegativity of which is given in parentheses (see "The Nature of the Chemical Bond" L. Pauling, 3rd Edition. 1960): Be (1.5), Mg (1.2), Al (1.5), Ga (1.6), In (1.7), Cu (1.9), Ag (1.9), La (1.1), Hf (1.3), Cr (1.6), Mo (1.8), Mn (1.5), Fe (1.8), Ru (2.2), Os (2.2), Co (1.8), Rh (2.2), Ir (2.2), Ni (1.8), Pd (2.2), Pt (2.2), and Ce (1.1). Preferred metallic cations are $Al^{3+}$, $In^{3+}$, $Cr^{3+}$, and the rare earth cations, particularly $La^{3+}$ and $Ce^{3+}$. Mixtures of two or more metallic cations having a Pauling electronegativity greater than 1.0 may be present in the catalyst in cation exchange positions on the surface of the hectorite-type mineral.

Representative synthetic trioctahedral 2:1 layer-lattice smectite-type minerals which are useful in this invention are the structural analogs of hectorite in which the central octahedral layer contains one or more divalent metals having an ionic radius not greater than 0.75 A, provided that the metal is less than 95 mole % Mg, preferably less than 90 mole % Mg.

The charge-balancing cations of the hectorite-type minerals which can be used to prepare the catalysts of the present invention must be cations capable of being exchanged, preferably $Na^+$, $Li^+$, or $NH_4^+$, unless they are metallic cations which have a Pauling electronegativity greater than 1.0.

The hectorite-type minerals useful in this invention can be synthesized hydrothermally. In general a gel containing the required molar ratios of the oxides or hydroxides of the metals desired to be incorporated into the central octahedral layer, silica, the charge balancing cations, and fluoride and having a pH of at least 8 is hydrothermally treated at a temperature within the range from 100° C–325° C, preferably 250° C – 300° C, and preferably at the autogenous water vapor pressure for a period of time sufficient to crystallize the desired hectorite, generally 12 – 72 hours depending on the temperature of reaction. In general as the reaction temperature decreases the reaction time increases for well crystallized hectorite-type minerals. The hectorite-type minerals can be crystallized from melts of the oxides at very high temperatures, generally greater than 950° C. In these processes the charge balancing cation must be too large to be incorporated into the layer lattices, generally greater than 0.75 A, except that the charge balancing cation may be $Li^+$. Preferably the charge balancing cation is $Na^+$ or $NH_4^+$ since these are readily removed by cation exchange and replaced with the metallic cation as required in the present inventive process and catalyst.

Hectorite-type clays can be represented by the structural formula:

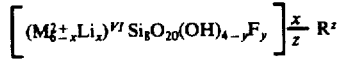

where the cations in the parentheses are the cations present in the central octahedral layer, the two outer tetrahedral layers contain the Si cations, and R represents the charge-balancing cations exterior to the layer lattice of valence z. In the preferred catalysts of the present invention:

M is divalent cation selected from the group consisting of Mg, Ni, Co, Zn, Mn, Cu, and mixture thereof, provided that M is less than 95 mole percent Mg(Mg<0.95(6-x));

R is at least one metallic cation which has a Pauling electronegativity greater than 1.0; and $$0.33 \leq x \leq 1$$

$$0 \leq y \leq 4$$

More preferably $0 \leq y \leq 2$ and M is selected from the group consisting of Mg, Ni, Co, and mixtures thereof.

The hectorite-type clays can contain minor amounts of other metals substituted isomorphously in the layer-lattices for the metals indicated in the above formulas, such as $Fe^{2+}$ and $Al^{3+}$ in the octahedral layer and $Al^{3+}$, and $Ge^{4+}$ in the tetrahedral layers. Metals having an ionic radius not greater than 0.75 A can be present in the octahedral layer. Metals having an ionic radius not greater than 0.64 A can be present in the tetrahedral layers. Generally the sum of such extraneous isomorphously substituted metals will amount to no more than 10 mole percent based on the metals present in the layer in which the substitution occurs.

The catalyst of the present invention can be prepared by any ion-exchange process wherein a metallic cation having a Pauling electronegativity greater than 1.0 can be made to replace the exchangeable cation of the hectorite-type clay. Preferably an aqueous solution of a soluble salt of the desired metallic cation is admixed with the desired hectorite-type clay for a period of time sufficient to effect the desired exchange. Preferably an amount of metallic cation will be used which is from 100% to 500% of the exchange capacity of the hectorite-type clay, more preferably 100% to 300%. It is preferred to exchange at least 50% of the exchangeable cations of the clay with the metallic cations of this invention. It is also preferred to remove excess metallic cation salt and the soluble salt by-products of the exchange from the catalyst such as by filtration and washing prior to drying the catalyst. Alternatively the excess metallic cation salt and soluble salt by-product can be removed from the dried catalyst by slurrying the catalyst in an appropriate solvent, such as water or methanol, followed by filtration and re-drying. The exchange can also be conducted using a solution of the metallic cation salt in an appropriate organic solvents, such as methanol. Alternatively, the process disclosed in U.S. Pat. No. 3,725,528 can be used to prepare the catalyst.

The catalyst of this invention has been found to be active in catalyzing the reaction between alkylatable aromatic hydrocarbons and olefin-acting compounds under anhydrous alkylating conditions in the liquid phase.

Alkylatable aromatic hydrocarbons which can be used in the inventive process include benzene, toluene, xylene, the naphthalene series of hydrocarbons, etc. Any aromatic hydrocarbon can be alkylated if it has an unsubstituted carbon as long as steric hindrance does not prevent alkylation with the particular olefin-acting compound chosen for use in the process, and as long as the alkyl side chains on the aromatic ring do not prevent the aromatic compound from being adsorbed onto the layer-lattice surfaces of the catalyst. Benzene is the preferred aromatic hydrocarbon.

The olefin-acting compounds may be selected from the group consisting of mono-olefins, alkyl bromides, alkyl chlorides, and mixtures thereof. Representative olefins include ethylene, propylene, 1-butene, 2-butene, 1-pentene, 2-pentene, 1-hexene, propylene tetramer, 1-octadecene, etc. Representative alkyl halides include n-butyl bromide, n-butyl chloride, n-dodecyl bromide, n-dodecyl chloride, etc.

The process is carried out in the liquid phase utilizing a catalytically effective amount of the catalyst hereinbefore described. The catalyst can be used in amounts from 1% to 100% by weight based on the olefin-acting compound depending on the particular metallic cation-exchanged hectorite-type catalyst chosen for the reaction, the temperature of the reaction, and the length of time the catalyst has been in service. Preferably a concentration of catalyst from 2% to 50% by weight is used since this gives a relatively fast alkylation, still more preferably 2% to 10%.

The pressure can be elevated and is not critical as long as some of the olefin-acting compound can be kept dissolved in the liquid aromatic phase. Thus the pressure should be correlated with the temperature at which the reaction is being carried out in order to maintain the aromatic hydrocarbon in the liquid phase and to maintain a sufficient amount of olefin-acting compound dissolved therein to allow the alkylation reaction to proceed. Atmospheric pressure is preferred because of the simplicity of operations under atmospheric conditions.

The process is conducted at an elevated temperature since the rate of alkylation is undesirably low at room temperature. Preferably the temperature is in the range from 40° C to 200° C, more preferably 70° C to 150° C. It is desirable to conduct the process at the boiling point (reflux temperature) of the alkylatable aromatic hydrocarbon provided that it is in the above noted range. A non-alkylatable solvent, such as cyclohexane, can be used to provide the liquid alkylating medium and the temperature can conveniently be maintained at the boiling point of the solvent.

The molar ratio of alkylatable aromatic hydrocarbon to alkylating agent, i.e., the olefin-acting compound, can vary widely depending on the product desired. Thus at higher ratios such as 10 or above essentially only mono-alkylated product is obtained whereas at lower ratios the amount of polyalkylated product is increased. Preferably a molar ratio within the range from 3:1 to 20:1 will be used, more preferably 5:1 to 10:1.

It is important to maintain the reaction system free of water since water has a deactivating effect on the catalyst. Thus the catalyst must be dried before use. This may conveniently be done by removing the water from the catalyst at a low temperature, i.e., less than about 200° C. Alternatively the water may be removed by azeotropic distillation from a mixture of the catalyst in the alkylatable aromatic hydrocarbon or the solvent to be used in the reaction. This method will also remove any water present in these organic systems and is preferred. The term "anhydrous" as used in this specification and in the claims is intended to mean that any free water which is present in the catalyst or the organic components present in the reaction mix is removed from the reaction system.

The following non-limiting examples are given in order to illustrate the invention.

EXAMPLES 1 – 27

Various cation exchanged forms of the natural mineral hectorite were prepared as follows: The exchange cation salt was dissolved in 500 to 750 ml. of methanol. Hectorite clay which had been previously dispersed in water, centrifuged, and spray dried in order to obtain the purified clay, was mixed in this salt solution at a concentration of 300 milliequivalents of cation per 100 grams of clay. This mixture was allowed to stand for approximately 20 hours before it was filtered. The filter cake was re-dispersed in 500 – 750 ml. of methanol followed by filtration for a total of 3 successive washings. The cation exchanged hectorite was then air dried for 20 hours at room temperature followed by oven drying at 105° C for 2 hours. The clay obtained by this process was very fine and needed no grinding. In the case of $Ag^+$-hectorite, 10 ml. of concentrated nitric acid was added to the methanol solution before adding the clay to the solution, in order to prevent oxide formation or hydrolysis of the $Ag+$.

These cation exchanged hectorite clays were evaluated as catalysts for the alkylation of benzene using the following procedure: 10 grams of the cation exchanged hectorite and 200 – 250 ml. of benzene are refluxed in a round bottom flask equipped with a Dean-Stark tube attached to remove, azeotropically, sorbed water from the clay. After 2 – 4 hours the tube was removed and the reflux condenser rinsed with methanol and air dried to remove any residual moisture trapped in the condenser. 10 grams of the alkylating agent was added to the flask and the mixture refluxed with stirring for 24 hours. The clay was removed by filtration and washed with 100 ml. of benzene. The benzene was removed from the filtrate by vacuum evaporation leaving a product of unreacted alkylating agent and/or alkylbenzene. This product was then weighed and analyzed by either infrared spectrophotometry, refractometry, or gas chromatography to determine the amount of alkyl-benzene formed. The cation exchanged hectorites evaluated and the data obtained are given in Table 1.

The data indicate that the natural hectorite clay containing exchanged metallic cations having a Pauling electronegativity less than or equal to 1.0 were ineffective as catalysts for the alkylation of benzene. Metallic cations having a Pauling electronegativity greater than 1.0 were effective catalysts when exchanged onto hectorite. These include $Be^{2+}$ and $Mg^{2+}$ (Group IIA), $Al^{3+}$ and $In^{3+}$ (Group IIIA), $La^{3+}$ (Group IIIB), $Cr^{3+}$ (Group VIA), $Mn^{2+}$ (Group VIIB), $Fe^{3+}$, $Co^{2+}$, $Ni^{2+}$ and $Pd^{2+}$ (Group VIII), $Cu^{2+}$ and $Ag^+$ (Group IB), and $Ce^{3+}$ (rare earths). The effect of moisture within the reaction zone on the activity of certain of the catalysts can be ascertained by reference to the data for Examples 1, 4 and 6. The small amount of water which remained in the reflux condenser (Examples 1,6) or in the atmosphere (Example 4) was sufficient to decrease the activity of $Al^{3+}$-exchanged hectorite approximately 50%, whereas $In^{3+}$-exchanged hectorite was very active in the presence of such small quantities of water.

TABLE 1

Alkylation of Benzene

Alkylating Agent: Catalyst Weight Ratio = 1:1
Benzene: Alkylating Agent Mole Ratio = 10:1
Temperature = 80.1° C (B.P. of Benzene)
Duration of Reaction = 24 Hours
Catalyst = Various Cation Exchanged Forms of Hectorite

| Example | Exchangeable Cation on Hectorite | Pauling Electronegativity of Cation | Alkylating Agent | % Yield of Alkylbenzene |
|---|---|---|---|---|
| 1  | $Al^{3+}$ | 1.5 | n-Butyl Bromide  | 80 (36)[a] |
| 2  | $In^{3+}$ | 1.7 | n-Butyl Bromide  | 86 |
| 3  | $H^+$     | 2.1 | n-Butyl Bromide  | 10 |
| 4  | $Al^{3+}$ | 1.5 | n-Butyl Chloride | 18 (40)[b] |
| 5  | $In^{3+}$ | 1.7 | n-Butyl Chloride | 94 |
| 6  | $Al^{3+}$ | 1.5 | Lauryl Bromide   | 89 (48)[a] |
| 7  | $In^{3+}$ | 1.7 | Lauryl Bromide   | (86)[a] |
| 8  | $Fe^{3+}$ | 1.8 | Lauryl Bromide   | (31)[a] |
| 9  | $Al^{3+}$ | 1.5 | 1-Octadecene | 93[c] |
| 10 | $In^{3+}$ | 1.7 | 1-Octadecene | 93[d] |
| 11 | $Al^{3+}$ | 1.5 | 1-Dodecene | 88 |
| 12 | $Fe^{3+}$ | 1.8 | 1-Dodecene | 88 |
| 13 | $Cr^{3+}$ | 1.6 | 1-Dodecene | 100 |
| 14 | $La^{3+}$ | 1.1 | 1-Dodecene | 100 |
| 15 | $Ce^{3+}$ | 1.1 | 1-Dodecene | 99 |
| 16 | $Be^{2+}$ | 1.5 | 1-Dodecene | 96 |
| 17 | $Mg^{2+}$ | 1.2 | 1-Dodecene | 96 |
| 18 | $Mn^{2+}$ | 1.5 | 1-Dodecene | 92 |
| 19 | $Co^{2+}$ | 1.8 | 1-Dodecene | 91 |
| 20 | $Ni^{2+}$ | 1.8 | 1-Dodecene | 93 |
| 21 | $Cu^{2+}$ | 1.9 | 1-Dodecene | 99 |
| 22 | $Pd^{2+}$ | 2.2 | 1-Dodecene | 71 |
| 23 | $Ag^+$    | 1.9 | 1-Dodecene | 100 |
| 24 | $Ca^{2+}$ | 1.0 | 1-Dodecene | 52 |
| 25 | $Ba^{2+}$ | 0.9 | 1-Dodecene | 5 |
| 26 | $Li^+$    | 1.0 | 1-Dodecene | 5 |
| 27 | $Na^+$    | 0.9 | 1-Dodecene | Trace[e] |

[a]Methanol Rinse of Reflux Condenser Omitted
[b]Nitrogen Circulated through the Reaction Flask
[c]Small Amount of n-Butyl Bromide Added to Promote the Reaction
[d]Small amount of Lauryl Bromide added to promote the reaction
[e]Clay without Exchange Treatment - Primarily $Na^+$ Form.

EXAMPLES 28 – 43

Several cation exchanged hectorites were prepared by at least one of the following procedures as indicated in Table 2: Process A — exchange in methanol solution as in Examples 1 - 27; Process B — exchange in aqueous solution substituting water for methanol in Process A except in the last washing step; Process C — exchange in aqueous solution, no washing. These catalysts were evaluated for the alkylation of benzene by 1-dodecene at a 1-dodecene:catalyst weight ratio of 10:1 using the same process as in Examples 1–27. The percent conversion of the olefin after one hour is given in Table 2. The catalysts used in Examples 33, 34, 37 and 38 were the same catalysts used in Examples 32, 33, 36 and 37 respectfully, after rinsing them with benzene.

The data indicate that water is the preferred solvent for the metallic cation salt, i.e., for the exchange solution, and that the catalyst should be washed to remove soluble salts from the catalyst. The catalyst can be re-used after rinsing with benzene to remove adsorbed products from the catalyst.

TABLE 2

Alkylation of Benzene with 1-Dodecene

Benzene: 1-Dodecene Mole Ratio = 10:1
1-Dodecene: Catalyst Weight Ratio: = 10:1
Temperature = 80.1° C (B.P. of Benzene)
Duration of Run = One Hour

| Example | Exchangeable Cation on Hectorite | 1-Dodecene to Cation Ratio | Catalyst Preparation Process | % Conversion of Olefin |
|---|---|---|---|---|
| 28 | $Al^{3+}$ | 1,000/1 | A | 53 |
| 29 | $Al^{3+}$ | 1,000/1 | B | 95 |
| 30 | $Al^{3+}$ | 1,000/1 | C | 1.2 |
| 31 | $Al^{3+}$ | 1,000/1 | C | 4.4 |
| 32 | $Al^{3+}$ | 1,000/1 | B | 97 |
| 33 | $Al^{3+}$ | 1,000/1 | B | 77[a] |
| 34 | $Al^{3+}$ | 1,000/1 | B | 37[b] |
| 35 | $Cr^{3+}$ | 526/1   | A | 90 |
| 36 | $Cr^{3+}$ | 526/1   | B | 99+ |
| 37 | $Cr^{3+}$ | 526/1   | B | 82[c] |
| 38 | $Cr^{3+}$ | 526/1   | B | 58[d] |
| 39 | $In^{3+}$ | 263/1   | A | 3 |
| 40 | $In^{3+}$ | 263/1   | B | 99 |
| 41 | $Mg^{2+}$ | 833/1   | A | 29 |
| 42 | $Fe^{3+}$ | 357/1   | B | 84 |
| 43 | $Ag^+$    | 256/1   | A | 21 |

[a]The catalyst from the previous experiment, after X hours reaction time and Y% conversion of dodecene, was re-used after it was rinsed with benzene, where X = 4 hours and Y = 99.3%.
[b]As [a], except X = 7 hours and Y = 99.1%
[c]As [a], except X = 1 hours and Y = 99+%
[d]As [a], except X = 3 hours and Y = 93.4%

EXAMPLES 44 – 54

An $Al^{3+}$-exchanged hectorite and a $Cr^{3+}$-exchanged hectorite (purified natural clay as in Examples 1 - 27) were prepared by the aqueous exchange process B of Examples 28 - 43. These clays were evaluated as catalysts for the alkylation of benzene by 1-dodecene at various mole ratios of benzene to dodecene and/or various weight ratios of dodecene to catalyst as indicated in Table 3. The percent conversion of dodecene after 1 hour and, in some cases, 24 hours using the same process as in Examples 1 - 27 was determined. The data obtained are given in Table 3.

The data indicate that these exchanged clays were excellent catalysts at concentrations of exchanged clay greater than about 2%, based on the weight of dodecene, although concentrations as low as 1% converted most of the dodecene in 24 hours.

15.8% of the 1-dodecene was converted to heavy alkylate.

Table 3

Alkylation of Benzene with 1-Dodecene
Benzene: 1-dodecene Mole Ratio: as indicated
1-dodecene: Catalyst Weight Ratio: as indicated
Temperature: 80.1° C (B.P. of Benzene)
Duration of Run: 1, 24 Hours
Catalyst: $Al^{3+}$- and $Cr^{3+}$-exchanged Hectorite as indicated

| Example | Exchangeable Cation on Hectorite | 1-dodecene to Catalyst Wt. Ratio | Benzene to 1-dodecene Mole Ratio | % Conversion of 1-dodecene 1 Hr. | 24 Hr. |
|---|---|---|---|---|---|
| 44 | $Cr^{3+}$ | 10:1 | 10:1 | 99.6 | — |
| 45 | $Cr^{3+}$ | 20:1 | 10:1 | 98.4 | — |
| 46 | $Cr^{3+}$ | 40:1 | 10:1 | 70.1 | — |
| 47 | $Cr^{3+}$ | 100:1 | 10:1 | 43.7 | 83.8 |
| 48 | $Al^{3+}$ | 10:1 | 10:1 | 97.0 | — |
| 49 | $Al^{3+}$ | 20:1 | 10:1 | 98.2 | — |
| 50 | $Al^{3+}$ | 40:1 | 10:1 | 82.1 | 99.0 |
| 51 | $Al^{3+}$ | 50:1 | 5:1 | 55.2 | 90.2 |
| 52 | $Al^{3+}$ | 100:1 | 10:1 | 34.2 | 78.0 |
| 53 | $Al^{3+}$ | 100:1 | 5:1 | 18.9 | 71.6 |
| 54 | $Al^{3+}$ | 100:1 | 20:1 | 29.6 | 67.1 |

EXAMPLE 55

A synthetic hectorite-type clay was prepared by reacting at a temperature of 350° C in a Ag-lined stainless steel autoclave under the autogenous water vapor pressure created in the autoclave for 48 hours a composition having the molar formula:

5.32 $NiCl_2$ . 0.68 LiCl . 8$SiO_2$ . 12 NaOH . 250 $H_2O$
(pH = 11.5)

The product obtained, after drying at 105° C, had x-ray diffraction peaks at 12.5 A and 1.517 A which indicates that the product was a well crystallized hectorite-type clay. The expected formula for this nickelferous hectorite is:

$[(Ni_{5.32}^{+2} Li_{0.68}^{+1})^{VI}(Si_8)^{IV} O_{20}(OH)_4]$ 0.68$Na^+$

This synthetic hectorite-type clay mineral was exchanged to the $Al^{3+}$-form as follows: the dried clay was mixed into an aqueous $AlCl_3$ solution at a concentration of 300 milliequivalents of $Al^{3+}$ per 100 grams of clay. The mixture was allowed to stand for approximately 20 hours before it was filtered. The filter cake was re-dispersed in 500–750 ml. of deionized water followed by filtration for a total of two successive washings. Thereafter another washing was undertaken substituting methanol for the deionized water. The $Al^{3+}$-cation exchanged hectorite-type clay was then air dried for 20 hours at room temperature followed by oven drying at 105° C for 2 hours. The catalyst obtained by this process was very fine and needed no grinding.

The $Al^{3+}$-exchanged synthetic hectorite-type clay was evaluated as follows: 1 gram of the clay and 200–500 ml. of benzene were refluxed in a round bottom flask equipped with a Dean-Stark tube attached to remove, azeotropically, sorbed water from the clay. After 2–4 hours the tube was removed and the reflux condenser rinsed with methanol and air dried to remove any residual moisture trapped in the condenser. 10 grams of 1-dodecene were then added to the flask and the mixture refluxed with stirring.

After 1 hour a sample was taken and analyzed by gas chromatographic analysis. 21.1% of the 1-dodecene was converted to dodecylbenzene and 9.8% of the 1-dodecene was converted to heavy alkylate. After 24 hours another sample was taken and analyzed. 67.5% of the 1-dodecene was converted to dodecylbenzene and

EXAMPLE 56

A synthetic hectorite-type clay was prepared by the process of Example 55 starting with a composition having the molar formula:

5.32 $CoCl_2$ . 0.68 LiCl . 8 $SiO_2$ . 12 NaOH.250 $H_2O$
(pH = 12.1)

The product obtained, after drying at 105° C, had x-ray diffraction peaks at 12.7 A and 1.522 A which indicates that the product was a well crystallized hectorite-type clay. The expected formula for this cobaltiferous hectorite is:

$[(Co_{5.32}^{2+} Li_{0.68}^{+})^{VI}(Si_8)^{IV} O_{20}(OH)_4]$ 0.68$Na^+$

This synthetic hectorite-type clay was exchanged to the $Al^{3+}$-form and evaluated as in Example 55. 48.1% of the 1-dodecene was converted to dodecylbenzene and 8.7% of the 1-dodecene was converted to heavy alkylate after 24 hours refluxing.

EXAMPLE 57

The procedures of Example 55 are repeated wherein the hectorite-type clay is exchanged with the following metallic cations: $Cr^{3+}$, $In^{3+}$, $Fe^{3+}$, $Ga^{3+}$, $Mn^{2+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, $Pt^{2+}$, and mixtures thereof.

Thus these catalysts have the following structural formula:

$[(Ni_{5.32}^{+2} Li_{0.68}^{+})^{VI}(Si_8)^{IV} O_{20}(OH)_4](0.68/z) R^z$ where $R^z$ = $Cr^{3+}$, $In^{3+}$, $Fe^{3+}$, $Ga^{3+}$, $Mn^{2+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, $Pt^{2+}$, and mixtures thereof.

EXAMPLE 58

The procedures of Example 55 are repeated wherein the autoclave feed composition has the molar formula:

2.66 Ni $Cl_2$ . 2.66 $CoCl_2$ . 0.68 Li F . 8 $SiO_2$. 12 NaOH.250$H_2O$

The formula for this nickeliferous-cobaltiferous hectorite-type clay is:

$[(Ni_{2.66}^{2+} Co_{2.66}^{2+} Li_{0.68}^{+})^{VI}(Si_8)^{IV} O_{20}(OH)_{3.32} F_{0.68}]$ 0.68 $Na^+$

The formula for the $Al^{3+}$-exchanged catalyst is:

$[(Ni_{2.66}{}^{2+} Co_{2.66}{}^{2+} Li_{0.68}{}^{+})^{IV}O_{20}(OH)_{3.32}F_{0.68}]\, 0.227\, Al^{3+}$

It will be understood that while I have explained the invention with the aid of specific examples, nevertheless considerable variation is possible in choice of raw materials, proportions, processing conditions, and the like, within the broad scope of the invention as set forth in the claims which follow. Thus, for example, my inventive catalyst may be used simultaneously with other catalytic materials so as to suit particular conditions and circumstances.

I claim:

1. In a process for alkylating in the liquid phase an alkylatable aromatic hydrocarbon with an olefin-acting compound selected from the group consisting of mono-olefins, alkyl bromides, alkyl chlorides, and mixtures thereof, the improvement which comprises contacting said hydrocarbon and said compound under anhydrous alkylating conditions with a catalyst comprising a synthetic hectorite-type clay in which the central octahedral layer contains one or more divalent metals having an ionic radius not greater than 0.75 A, provided that the octahedral layer contains less than 95 mole percent Mg, containing a metallic cation having a Pauling electronegativity greater than 1.0 in cation exchange positions on the surface of said clay.

2. The process of claim 1 wherein said catalyst has the structural formula:

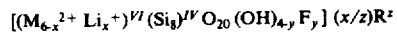
$[(M_{6-x}{}^{2+} Li_x{}^+)^{VI}(Si_8)^{IV}O_{20}(OH)_{4-y}F_y]\,(x/z)R^z$ where $0.33 \leq x \leq 1$ $0 \leq y \leq 4$ M is one or more divalent cations having an ionic radius not greater than 0.75 A selected from the group consisting of Mg, Ni, Co, Zn, Mn, and Cu, and R is at least one metallic cation having a Pauling electronegativity greater than 1.0 of valence z.

3. The process of claim 2 wherein $0 \leq y \leq z$ and wherein M is a divalent cation selected from the group consisting of Mg, Ni, Co, and mixtures thereof.

4. The process of claim 3 wherein M is less than 90 mole percent Mg.

5. The process of claim 4 wherein said aromatic hydrocarbon is benzene and wherein said olefin-acting compound is a mono-olefin.

6. The process of claim 5 wherein said mono-olefin is 1-dodecene.

7. The process of claim 6 wherein said R is $Al^{3+}$.

8. The process of claim 4 wherein said R is selected from the group consisting of $Al^{3+}$, $Cr^{3+}$, $Ga^{3+}$, $In^{3+}$, $Mn^{2+}$, $Fe^{3+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, and mixtures thereof.

9. The process of claim 4 wherein said R is $Al^{3+}$.

10. A process for alkylating aromatic hydrocarbons which comprises contacting in the liquid phase an alkylatable aromatic hydrocarbon with a mono-olefin under alkylating conditions in a reaction zone which is substantially free of water and in the presence of an effective amount of a catalyst, said catalyst comprising a synthetic hectorite-type clay containing a metallic cation having a Pauling electronegativity greater than 1.0 in cation exchange positions on the surface of said clay, said catalyst having the following structural formula:

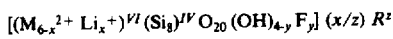
$[(M_{6-x}{}^{2+} Li_x{}^+)^{VI}(Si_8)^{IV}O_{20}(OH)_{4-y}F_y]\,(x/z)R^z$ where $0.33 \leq x \leq 1$ $0 \leq y \leq 4$ M is one or more divalent cations having an ionic radius not greater than 0.75 A, provided that M is less than 95 mole percent Mg, and R is at least one of said metallic cations having a Pauling electronegativity greater than 1.0 of valence z.

11. The process of claim 10 wherein $0 \leq y \leq 2$ and wherein M is selected from the group consisting of Mg, Ni, Co, and mixtures thereof.

12. The process of claim 11 wherein M is less than 90 mole percent Mg.

13. The process of claim 12 wherein said aromatic hydrocarbon is benzene and wherein said olefin-acting compound is a mono-olefin.

14. The process of claim 13 wherein said mono-olefin contains twelve carbon atoms.

15. The process of claim 14 wherein said R is $Al^{3+}$.

16. The process of claim 12 wherein said R is selected from the group consisting of $Al^{3+}$, $Cr^{3+}$, $Ga^{3+}$, $In^{3+}$, $Mn^{2+}$, $Fe^{3+}$, $Co^{3+}$, $Co^{2+}$, $Ni^{2+}$, $Cu^{2+}$, $Ag^+$, $Be^{2+}$, $Mg^{2+}$, $La^{3+}$, $Ce^{3+}$, $Pd^{2+}$, and mixtures thereof.

17. The process of claim 12 wherein said R is $Al^{3+}$.

* * * * *